US006939702B1

(12) United States Patent
Vind et al.

(10) Patent No.: US 6,939,702 B1
(45) Date of Patent: Sep. 6, 2005

(54) LIPASE VARIANT

(75) Inventors: Jesper Vind, Lyngby (DK); Allan Svendsen, Birkerød (DK); Shamkant Anant Patkar, Lyngby (DK); Kim Vilbour Andersen, Copenhagen (DK); Dorte Aaby Halkier, Birkerød (DK); Kirsten Bojsen, Hellerup (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/937,919

(22) PCT Filed: Mar. 30, 2000

(86) PCT No.: PCT/DK00/00156

§ 371 (c)(1),
(2), (4) Date: Oct. 1, 2001

(87) PCT Pub. No.: WO00/60063

PCT Pub. Date: Oct. 12, 2000

Related U.S. Application Data

(60) Provisional application No. 60/128,933, filed on Apr. 13, 1999.

(30) Foreign Application Priority Data

Mar. 31, 1999 (DK) ........................................ 1999 00441

(51) Int. Cl.⁷ .............................. C12N 9/20; C07H 21/04

(52) U.S. Cl. ................ 435/198; 435/252.3; 435/252.33; 435/320.1; 510/114; 536/23.1; 536/23.2

(58) Field of Search ............................... 435/198, 252.3, 435/252.33, 320.1; 536/23.1, 23.2; 510/114

(56) References Cited

FOREIGN PATENT DOCUMENTS

| EP | 0 258 068 | 3/1988 |
|----|-----------|--------|
| EP | 0 305 216 | 3/1995 |
| WO | 92/05249 | 4/1992 |
| WO | 94/25577 | 11/1994 |
| WO | WO 95/22615 | 8/1995 |
| WO | 97/04079 | 2/1997 |
| WO | WO 97/07202 | 2/1997 |
| WO | WO 99/42566 | 8/1999 |
| WO | WO 00/60063 | 10/2000 |

*Primary Examiner*—Nashaat T. Nashed
(74) *Attorney, Agent, or Firm*—Jason Garbeu; Elias Lambins

(57) ABSTRACT

Certain variants of Lipolase (wild-type *Humicola lanuginosa* lipase) have a particularly good first-wash performance in a detergent solution. The variants should comprise one or more substitutions with positive amino acids near the N-terminal in the three-dimensional structure. The variants should further comprise a peptide addition at the C-terminal and/or should meet certain limitations on electrically charged amino acids at positions 90–101 and 210.

26 Claims, No Drawings

SEQUENCE LISTING

<160> NUMBER OF SEQ ID NOS: 1

<210> SEQ ID NO 1
<211> LENGTH: 269
<212> TYPE: PRT
<213> ORGANISM: Humicola lanuginosa

<400> SEQUENCE: 1

```
Glu Val Ser Gln Asp Leu Phe Asn Gln Phe Asn Leu Phe Ala Gln Tyr
  1               5                  10                  15

Ser Ala Ala Ala Tyr Cys Gly Lys Asn Asn Asp Ala Pro Ala Gly Thr
             20                  25                  30

Asn Ile Thr Cys Thr Gly Asn Ala Cys Pro Glu Val Glu Lys Ala Asp
         35                  40                  45

Ala Thr Phe Leu Tyr Ser Phe Glu Asp Ser Gly Val Gly Asp Val Thr
     50                  55                  60

Gly Phe Leu Ala Leu Asp Asn Thr Asn Lys Leu Ile Val Leu Ser Phe
 65                  70                  75                  80

Arg Gly Ser Arg Ser Ile Glu Asn Trp Ile Gly Asn Leu Asn Phe Asp
                 85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
            115                 120                 125

Glu Asp Ala Val Arg Glu His Pro Asp Tyr Arg Val Val Phe Thr Gly
        130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
```

-continued

```
            210                 215                 220
Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
                260                 265
```

LIPASE VARIANT

CROSS-REFERENCE TO RELATED APPLICATIONS

This application is a 35 U.S.C. 371 national application of PCT/DK00/00156, filed Mar. 30, 2000, (the international application was published under PCT Article 21(2) in English) and claims, under 35 U.S.C. 119, priority of Danish application no. PA 1999 00441, filed Mar. 31, 1999, and benefit of U.S. provisional application no. 60/128,933, filed Apr. 13, 1999, the contents of which are fully incorporated herein by reference.

FIELD OF THE INVENTION

The present invention relates to lipase variants suited for use in detergent compositions. More particularly, the invention relates to variants of the wild-type lipase from *Humicola lanuginosa* strain DSM 4109 showing a first-wash effect.

BACKGROUND OF THE INVENTION

For a number of years, lipases have been used as detergent enzymes to remove lipid or fatty stains from clothes and other textiles, particularly a lipase derived from *Humicola lanuginosa* (EP 258 068 and EP 305 216) sold under the tradename Lipolase® (product of Novo Nordisk A/S).

WO 92/05249, WO 94/25577, WO 95/22615, WO 97/04079 and WO 97/07202 disclose variants of the *H. lanuginosa* lipase having improved properties for detergent purposes. Thus, WO 97/04079 discloses variants having a peptide addition (extension) at the N-terminal and/or the C-terminal. WO 97/07202 discloses lipase variants with "first wash performance" which are capable of removing substantial amounts of lard from a lard stained swatch in a one-cycle wash.

There is an ever existing need for providing novel lipases with improved washing properties in a variety of commercial detergents. The present invention relates to such novel lipases.

SUMMARY OF THE INVENTION

The inventors have found that certain variants of Lipolase (wild-type *Humicola lanuginosa* lipase) have a particularly good first-wash performance in a detergent solution. The lipases may further provide additional benefits, such as whiteness maintenance and dingy cleanup.

The inventors found that the variants should comprise one or more substitutions with positive amino acids near the N-terminal in the three-dimensional structure. The variants should further comprise a peptide addition at the C-terminal and/or should meet certain limitations on electrically charged amino acids at positions 90–101 and 210.

Accordingly, the invention provides a lipase which is a polypeptide having an amino acid sequence which:
  a) has at least 90% identity with the wild-type lipase derived from *Humicola lanuginosa* strain DSM 4109;
  b) compared to said wild-type lipase, comprises a substitution of an electrically neutral or negatively charged amino acid at the surface of the three-dimensional structure within 15 Å of E1 or Q249 with a positively charged amino acid; and
  c) comprises a peptide addition at the C-terminal; and/or
  d) meets the following limitations:
    i) comprises a negative amino acid in position E210 of said wild-type lipase;
    ii) comprises a negatively charged amino acid in the region corresponding to positions 90–101 of said wild-type lipase; and
    iii) comprises a neutral or negative amino acid at a position corresponding to N94 of said wild-type lipase and/or has a negative or neutral net electric charge in the region corresponding to positions 90–101 of said wild-type lipase.

DETAILED DESCRIPTION OF THE INVENTION

*Humicola lanuginosa* Lipase

The reference lipase used in this invention is the wild-type lipase derived from *Humicola lanuginosa* strain DSM 4109 having the amino acid sequence of SEQ ID NO:1. It is described in EP 258 068 and EP 305 216 and has the amino acid sequence shown in positions 1–269 of SEQ ID NO: 2 of U.S. Pat. No. 5,869,438. In this specification, the reference lipase is also referred to as Lipolase.

Substitution with Positive Amino Acid

The lipase of the invention comprises one or more (e.g. 2–4, particularly two) substitutions of an electrically neutral or negatively charged amino acid near E1 or Q249 with a positively charged amino acid, preferably R.

The substitution is at the surface of the three-dimensional structure within 15 Å of E1 or Q249, e.g. at any of positions 1–11, 90, 95, 169, 171–175, 192–211, 213–226, 228–258, 260–262.

The substitution may be within 10 Å of E1 or Q249, e.g. at any of positions 1–7, 10, 175, 195, 197–202, 204–206, 209, 215, 219–224, 230–239, 242–254.

The substitution may be within 15 Å of E1, e.g. at any of positions 1–11, 169, 171, 192–199, 217–225, 228–240, 243–247, 249, 261–262.

The substitution is most preferably within 10 Å of E1, e.g. at any of positions 1–7, 10, 219–224 and 230–239.

Thus, some preferred substitutions are S3R, S224R, P229R, T231R, N233R, D234R and T244R.

Peptide Addition at C-terminal

The lipase may comprise a peptide addition attached to C-terminal L269. The peptide addition improves the first-wash performance in a variety of detergents.

The peptide addition preferably consists of 1–5 amino acids, e.g. 2, 3 or 4 amino acids. The amino acids of the peptide addition will be numbered 270, 271, etc.

The peptide addition may consist of electrically neutral (e.g. hydrophobic) amino acids, e.g. PGL or PG. In an alternative embodiment, the lipase peptide addition consists of neutral (e.g. hydrophobic) amino acids and the amino acid C, and the lipase comprises substitution of an amino acid with C at a suitable location so as to form a disulfide bridge with the C of the peptide addition. Examples are:

270C linked to G23C or T37C
  271C linked to K24C, T37C, N26C or R81C
  272C linked to D27C, T35C, E56C, T64C or R81C.

Amino Acids at Positions 90–101 and 210

The lipase of the invention preferably meets certain limitations on electrically charged amino acids at positions 90–101 and 210. Lipases meeting the charge limitations are particularly effective in a detergent with high content of anionic.

Thus, amino acid 210 may be negative. E210 may be unchanged or it may have the substitution E210D/C/Y, particularly E210D.

The lipase may comprise a negatively charged amino acid at any of positions 90–101 (particularly 94–101), e.g. at position D96 and/or E99.

Further, the lipase may comprise a neutral or negative amino acid at position N94, i.e. N94 (neutral or negative), e.g. N94N/D/E.

Also, the lipase may have a negative or neutral net electric charge in the region 90–101 (particularly 94–101), i.e. the number of negative amino acids is equal to or greater than the number of positive amino acids. Thus, the region may be unchanged from Lipolase, having two negative amino acids (D96 and E99) and one positive (K98), and having a neutral amino acid at position 94 (N94), or the region may be modified by one or more substitutions.

Alternatively, two of the three amino acids N94, N96 and E99 may have a negative or unchanged electric charge. Thus, all three amino acids may be unchanged or may be changed by a conservative or negative substitution, i.e. N94 (neutral or negative), D (negative) and E99 (negative). Examples are N94D/E and D96E. Also, one of the three may be substituted so as to increase the electric charge, i.e. N94 (positive), D96 (neutral or positive) or E99 (neutral or positive). Examples are N94K/R, D96I/L/N/S/W or E99N/Q/K/R/H.

The substitution of a neutral with a negative amino acid (N94D/E), may improve the performance in an anionic detergent. The substitution of a neutral amino acid with a positive amino acid (N94K/R) may provide a variant lipase with good performance both in an anionic detergent and in an anionic/non-ionic detergent (a detergent with e.g. 40–70% anionic out of total surfactant).

Amino Acids at Other Positions

The inventors have found that a substitution Q249R/K/H may improve the performance both in anionic and in anionic/non-ionic detergent, and that a substitution of R209 with a neutral or negative amino acid (e.g. R209P/S) may improve the performance in anionic detergent. The lipase may optionally comprise the substitution G91A.

The lipase may optionally comprise substitutions of one or more additional amino acids. Such substitutions may, e.g., be made according to principles known in the art, e.g. substitutions described in WO 92/05249, WO 94/25577, WO 95/22615, WO 97/04079 and WO 97/07202.

Combinations of Substitutions

A lipase variant with good first-wash performance may be obtained by modifying Lipolase as follows. Substitutions in parentheses are optional.

T231R + N233R
N94K + D96L + T231R + N233R + Q249R + 270P + 271G + 272L
D96L + T231R + N233R
G91A + E99K + T231R + N233R + Q249R
(N33Q) + D96L + T231R + N233R + Q249R + 270 PGL
R209P + T231R + N233R
(N33Q) + E99N + N101S + T231R + N233R + Q249R + 270 PGL
K24C + (N33Q) + D96S + T231R + N233R + Q249R + 270 PCL
(N33Q) + G91A + E99K + T231R + N233R + Q249R + 270 PGL
E1A + (N33Q) + G91A + E99K + T231R + N233R + Q249R + 270 PGL
(N33Q) + G91A + E99K + G255R + T231R + N233R + Q249R + 270 PGL
(N33Q) + G91A + E99K + T231R + N233R + T244R + Q249R + 270 PGL
G91A + E99K + T231R + N233R + Q249R
EB7K + G91D + D96L + G225P + T231R + N233R + Q249R + N251D
G91A + E99K + T231R + N233R + Q249R + 270AGVF
G91A + E99K + T189G + T231R + N233R + Q249R
D102G + T231R + N233R + Q249R
T231R + N233R + Q249R + 270AGVF
R209P + T231R + N233R
N33Q + N94K + D96L + T231R + N233R + Q249R + 270PGLPFKRV
N33Q + N94K + Q96L + T231R + N233R + Q249R
N33Q + D96S + T231R + N233R + Q249R
N33Q + D965 + V2281 + + T231R + N233R + Q249R
E1A + N330 + G91A + E99K + T231R + N233R + Q249R + 270PGLPFKRV
N33Q + S83T + E87K + G91A + E99K + T231R + N233R + Q249R + 270PGLPFKRV
N33Q + G91A + E99K + T231R + N233R + Q249R + 270PGLPFKRV
T231R + N233R + 270CP
T231R + N233R + 270RE
N33Q + E99N + N101S + T231R + N233R + Q249R + 270PGLPFKRV

-continued

062A + S83T + G91A + E99K + T231R + N233R + Q249R
E99N + N101S + T231R + N233R + Q249R
R84W + G91A + E99K + T231R + N233R + Q249R
G91A + E99K + T231R + N233R + Q249R + 270SPG
G91A + E99K + T231R + N233R + Q249R + 270VVVP
G91A + E99K + T231R + N233R + Q249R + 270LLASSGRGGHR
G91A + E99K + T231R + N233R + Q249R + 270VTT
G91A + E99K + T231R + N233R + Q249R + 270VLQ
G91A + E99K + T231R + N233R + Q249R + 270T5T
G91A + E99K + T231R + N233R + Q249R + 270LR1
V60G + D62E + G91A + E99K + T231R + N233R + Q249R
G91A + D96W + E99K + T231R + N233R + G263Q + L264A + I265T + G266S + T267A + L269N + 270AGGFS

Nomenclature for Amino Acid Modifications

The nomenclature used herein for defining mutations is essentially as described in WO 92/05249. Thus, T231R indicates a substitution of T in position 231 with R. PGL or 270P+ 271G+ 272L indicates the peptide addition PGL attached to the C-terminal (L269).

Amino Acid Grouping

In this specification, amino acids are classified as negatively charged, positively charged or electrically neutral according to their electric charge at pH 10, which is typical of the detergent of the invention. Thus, negative amino acids are E, D, C (cysteine) and Y, particularly E and D. Positive amino acids are R, K and H, particularly R and K. Neutral amino acids are G, A, V, L, I, P, F, W, S, T, M, N, Q and C when forming part of a disulfide bridge. A substitution with another amino acid in the same group (negative, positive or neutral) is termed a conservative substitution.

The neutral amino acids may be divided into hydrophobic (G, A, V, L, I, P, F, W and C as part of a disulfide bridge) and hydrophilic (S, T, M, N, Q).

Amino Acid Identity

The lipase variant of the of the invention has an amino acid identity of at least 90% (preferably more than 95% or more than 98%) with Lipolase.

The degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–45), using GAP with the following settings for polypeptide sequence comparison: GAP creation penalty of 3.0 and GAP extension penalty of 0.1.

DNA Sequence, Expression Vector, Host Cell, Production of Lipase

The invention provides a DNA sequence encoding the lipase of the invention, an expression vector harboring the DNA sequence, and a transformed host cell containing the DNA sequence or the expression vector. These may be obtained by methods known in the art.

The invention also provides a method of producing the lipase by culturing the transformed host cell under conditions conducive for the production of the lipase and recovering the lipase from the resulting broth. The method may be practiced according to principles known in the art.

Detergent Additive

According to the invention, the lipase may typically be used as an additive in a detergent composition. This additive is conveniently formulated as a non-dusting granulate, a stabilized liquid, a slurry or a protected enzyme. The additive may be prepared by methods known in the art.

DETERGENT COMPOSITION

The detergent compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The detergent composition of the invention comprises the lipase of the invention and a surfactant. Additionally, it may optionally comprise a builder, another enzyme, a suds suppresser, a softening agent, a dye-transfer inhibiting agent and other components conventionally used in detergents such as soil-suspending agents, soil-releasing agents, optical brighteners, abrasives, bactericides, tarnish inhibitors, coloring agents, and/or encapsulated or non-encapsulated perfumes.

The detergent composition according to the invention can be in liquid, paste, gels, bars or granular forms. The pH (measured in aqueous solution at use concentration) will usually be neutral or alkaline, e.g. in the range of 7–11, particularly 9–11. Granular compositions according to the present invention can also be in "compact form", i.e. they may have a relatively higher density than conventional granular detergents, i.e. form 550 to 950 g/l.

The lipase of the invention, or optionally another enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

The detergent composition of the invention may comprise the lipase in an amount corresponding to 10–50,000 LU per gram of detergent, preferably 20–5,000 LU/g, e.g. 100–1000 LU/g. The detergent may be dissolved in water to produce a wash liquor containing lipolytic enzyme in an amount corresponding to 25–15,000 LU per liter of wash liquor, particularly 100–5000 LU/l, e.g. 300–2000 LU/l. The amount of lipase protein may be 0.001–10 mg per gram of detergent or 0.001–100 mg per liter of wash liquor.

More specifically, the lipase of the invention may be incorporated in the detergent compositions described in WO 97/04079, WO 97/07202, WO 97/41212, PCT/DK WO 98/08939 and WO 97/43375.

Surfactant System

The surfactant system may comprise nonionic, anionic, cationic, ampholytic, and/or zwitterionic surfactants. As described above, the lipase variants of the invention are particularly suited for detergents comprising of a combination of anionic and nonionic surfactant with 70–100% by weight of anionic surfactant and 0–30% by weight of nonionic, particularly 80–100% of anionic surfactant and 0–20% nonionic. As further described, some preferred lipases of the invention are also suited for detergents comprising 40–70% anionic and 30–60% non-ionic surfactant.

The surfactant is typically present at a level from 0.1% to 60% by weight, e.g. 1% to 40%, particularly 10–40%. preferably from about 3% to about 20% by weight. Some examples of surfactants are described below.

Anionic Surfactants

Preferred anionic surfactants include alkyl sulfate, alkyl ethoxy sulfate, linear alkyl benzene sulfonate and mixtures of these.

The alkyl sulfate surfactants are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium.

Alkylbenzene sulfonates are suitable, especially linear (straight-chain) alkyl benzene sulfonates (LAS) wherein the alkyl group preferably contains from 10 to 18 carbon atoms.

Suitable anionic surfactants include alkyl alkoxylated sulfates which are water soluble salts or acids of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like.

Other anionic surfactants include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates.

Nonionic Surfactant

The surfactant may comprise polyalkylene oxide (e.g. polyethylene oxide) condensates of alkyl phenols. The alkyl group may contain from about 6 to about 14 carbon atoms, in a straight chain or branched-chain. The ethylene oxide may be present in an amount equal to from about 2 to about 25 moles per mole of alkyl phenol.

The surfactant may also comprise condensation products of primary and secondary aliphatic alcohols with about 1 to about 25 moles of ethylene oxide. The alkyl chain of the aliphatic alcohol can either be straight or branched, and generally contains from about 8 to about 22 carbon atoms.

Further, the nonionic surfactant may comprise polyethylene oxide condensates of alkyl phenols, condensation products of primary and secondary aliphatic alcohols with from about 1 to about 25 moles of ethylene oxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Preferred nonionic surfactants are alcohol ethoxylate, alcohol phenol ethoxylate, polyhydroxy fatty acid amide, alkyl polyglucoside and mixtures of these.

EXAMPLE

First-wash Performance at Various Dosages in Anionic Detergent

The following 5 variants according to the invention were prepared and tested with 3 types of soiled swatches, and the parent lipase was included for comparison:

T231R + N233R.
G91A + D96W + E99K + G263Q +L264A + I265T + G266D + T267A +L269N + 270AGGFSWRRYRSAESVDKRATMTDAELEKKLNSYVQMDKEYVKNNQARS
R209P + T231R + N233R
N33Q + D96S + T231R + N233R + Q249R
E99N + N101S + T231R + N233R + Q249R

A commercial US detergent with a high content of anionic surfactant was heated to inactivate the enzymes already present, and was used at 1.4 g/l in a Tergot-o-meter™ laboratory washing machine. The water hardness was 6° dH (Ca:Mg 2:1), and the washing conditions were 1 cycle at 30° C. for 12 minutes, followed by over-night drying on filter paper. The lipase variant was added at dosages of 6400 and 12800 LU/l. Double determinations were made in two separate washes (same TOM).

The following three types of textile swatches tested were: Lard/Sudan Red on cotton Style 400, freshly prepared; wfk 20-LS Lipstick on polyester/cotton; and wfk 10-LS lipstick on cotton. The soil removal was evaluated by measuring the remission at 460 nm after the first washing cycle, and the results were expressed as $\Delta R$ by subtracting the remission of a blank without enzyme.

The results were that each variant at each dosage showed an improved first-wash performance on each type of soiled swatch ($\Delta R$ of 5 to 13), whereas the parent enzyme had essentially no effect ($\Delta R=0\pm2$) under the same conditions.

What is claimed is:

1. A lipase which is a polypeptide having an amino acid sequence which has at least 90% identity to SEQ ID NO:1 and which comprises a substitution of an electrically neutral or negatively charged amino acid with R or K at a position corresponding to any of positions 3, 224, 229 and 233 in SEQ ID NO:1 and comprises:
   i) a negative amino acid at a position corresponding to position E210 in SEQ ID NO:1;
   ii) a negatively charged amino acid in the region corresponding to positions 90–101 in SEQ ID NO:1; and
   iii) a neutral or negative amino acid at a position corresponding to N94 in SEQ ID NO:1 and/or has a negative or neutral net electric charge in the region corresponding to positions 90–101 in SEQ ID NO:1.

2. The lipase of claim 1, wherein said substitution is at a position corresponding to position 3 in SEQ ID NO:1.

3. The lipase of claim 1, wherein said substitution is at a position corresponding to position 224 in SEQ ID NO:1.

4. The lipase of claim 1, wherein said substitution is at a position corresponding to position 229 in SEQ ID NO:1.

5. The lipase of claim 1, wherein said substitution is at a position corresponding to position 233 in SEQ ID NO:1.

6. The lipase of claim 1, wherein said lipase further comprises a substitution of an R or K at a position corresponding to position 231 in SEQ ID NO:1.

7. The lipase of claim 1, wherein said lipase further comprises a substitution of an R or K at a position corresponding to position 244 in SEQ ID NO:1.

8. The lipase of claim 1, wherein the lipase has at least 95% identity to SEQ ID NO:1.

9. The lipase of claim 1, wherein the lipase has at least 98% identity to SEQ ID NO:1.

10. The lipase of claim 1, wherein said substitution is a substitution of R at a position corresponding to any of positions 3, 224, 229 and 233 in SEQ ID NO:1.

11. The lipase of claim 1, wherein said substitution is a substitution of K at a position corresponding to any of positions 3, 224, 229, and 233 in SEQ ID NO:1.

12. The lipase of claim 1, wherein said substitution is a substitution of R at a position corresponding to position 233 in SEQ ID NO:1 and said lipase further comprises a substitution of R or K at a position corresponding to position 231 in SEQ ID NO:1.

13. The lipase of claim 1, wherein said substitution is a substitution of K at a position corresponding to position 233 in SEQ ID NO:1 and said lipase further comprises a substitution of R or K at a position corresponding to position 231 in SEQ ID NO:1.

14. The lipase of claim 1, wherein said lipase further comprises a peptide addition at the C-terminal.

15. The lipase of claim 14, wherein the peptide addition consists of 1–5 amino acids.

16. The lipase of claim 14, wherein the peptide addition consists of electrically neutral amino acids.

17. The lipase of claim 14, wherein the peptide addition consists of neutral amino acids and a cysteine.

18. The lipase of claim 14, which comprises amino acids which either have a negative charge or are neutral in at least two of positions corresponding to positions N94, D96 and E99 in SEQ ID NO:1.

19. A detergent composition comprising a surfactant and the lipase of claim 1.

20. The detergent composition of claim 19, wherein the surfactant comprises anionic surfactant in an amount of more than 70% by weight of the total surfactant.

21. The detergent composition of claim 19, wherein the surfactant comprises an anionic surfactant in an amount of 40–70% by weight and nonionic surfactant in an amount of 30–60% by weight of the total surfactant, and the lipase is the lipase of claim 1.

22. The detergent composition of claim 19 which comprises 10–40% by weight of a surfactant.

23. A DNA sequence encoding the lipase of claim 1.

24. An expression vector comprising the DNA sequence of claim 23.

25. A transformed host cell comprising the DNA sequence of claim 23.

26. A method for producing a lipase, which method comprises culturing the transformed host cell of claim 25 under conditions conducive for the production of the lipase and recovering the lipase from the resulting broth.

* * * * *